United States Patent
Flores-Candia et al.

(10) Patent No.: US 9,283,161 B2
(45) Date of Patent: Mar. 15, 2016

(54) AQUEOUS COSMETIC COMPOSITIONS CONTAINING RESVERATROL SOLUBILIZED IN A LIQUID PHOSPHATE ESTER SURFACTANT

(71) Applicant: DSM IP ASSETS B.V., Heerlen (NL)

(72) Inventors: Juana-Lucia Flores-Candia, Basel (CH); Karina Hecker, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/347,155

(22) PCT Filed: Sep. 24, 2012

(86) PCT No.: PCT/EP2012/068748
§ 371 (c)(1),
(2) Date: Mar. 25, 2014

(87) PCT Pub. No.: WO2013/045384
PCT Pub. Date: Apr. 4, 2013

(65) Prior Publication Data
US 2014/0235731 A1    Aug. 21, 2014

(30) Foreign Application Priority Data

Sep. 26, 2011 (EP) .................................... 11182714

(51) Int. Cl.
| | | |
|---|---|---|
| *A61K 8/27* | (2006.01) | |
| *A61K 8/34* | (2006.01) | |
| *A61K 8/37* | (2006.01) | |
| *A61K 8/55* | (2006.01) | |
| *A61Q 19/02* | (2006.01) | |
| *A61K 8/06* | (2006.01) | |
| *A61K 8/39* | (2006.01) | |

(52) U.S. Cl.
CPC . *A61K 8/37* (2013.01); *A61K 8/062* (2013.01); *A61K 8/347* (2013.01); *A61K 8/375* (2013.01); *A61K 8/39* (2013.01); *A61K 8/55* (2013.01); *A61Q 19/02* (2013.01); *A61K 2800/49* (2013.01)

(58) Field of Classification Search
CPC ......... A61K 8/347; A61K 8/37; A61K 8/375; A61K 8/556; A61K 8/0295; A61K 8/062; A61K 8/342; A61K 2800/52; A61Q 19/002; A61Q 19/00; A61Q 19/08; A61Q 17/04; A61Q 1/02
USPC ............................ 424/401; 514/733; 558/186
See application file for complete search history.

(56) References Cited

U.S. PATENT DOCUMENTS

| | | | |
|---|---|---|---|
| 2004/0175347 A1 | 9/2004 | Bissett | |
| 2006/0269494 A1* | 11/2006 | Gupta | ........................ 424/70.1 |
| 2010/0028317 A1* | 2/2010 | Maes | .................... A61K 8/347 424/94.1 |
| 2011/0171288 A1* | 7/2011 | Mohammadi | ........ A61K 8/0295 424/450 |

FOREIGN PATENT DOCUMENTS

| | | |
|---|---|---|
| DE | 10 2006 027138 | 12/2007 |
| EP | 1 234 571 | 8/2002 |
| FR | 2 777 183 | 10/1999 |
| FR | 2 923 717 | 5/2009 |
| WO | WO 01/30336 | 5/2001 |

OTHER PUBLICATIONS

International Search Report for PCT/EP2012/068748, mailed Oct. 25, 2012.

\* cited by examiner

*Primary Examiner* — Blessing M Fubara
(74) *Attorney, Agent, or Firm* — Nixon & Vanderhye P.C.

(57) ABSTRACT

The present invention relates to a fluid composition comprising water and a self-emulsifying cosmetic base consisting of resveratrol, a liquid phosphate ester surfactant, at least one cosmetic oil and optionally a co-emulsifier. The present invention also relates to the process to make such fluids.

14 Claims, No Drawings

AQUEOUS COSMETIC COMPOSITIONS CONTAINING RESVERATROL SOLUBILIZED IN A LIQUID PHOSPHATE ESTER SURFACTANT

This application is the U.S. national phase of International Application No. PCT/EP2012/068748, filed 24 Sep. 2012, which designated the U.S. and claims priority to EP Application No. 11182714.3, filed 26 Sep. 2011, the entire contents of each of which are hereby incorporated by reference.

The present invention relates to a fluid composition comprising water and a self-emulsifying cosmetic base consisting of resveratrol, a liquid phosphate ester surfactant, at least one cosmetic oil and optionally a co-emulsifier. The present invention also relates to the process to make such fluid compositions.

Skin Care market is evolving toward cosmetic compositions with enhanced skin whitening properties as consumers are expressing strong interest in achieving uniform and lighter skin tone. Solar lentigos, post-inflammatory hyperpigmentation and melasma are skin disorder widely distributed in human population. Furthermore, the skin lightening market is one of the cosmetic market segments showing the biggest growth; driven largely by expanding Asian markets, as well as by extension of skin whitening products to specific consumer segments (i.e., men care). Different products exhibiting skin whitening activities exist in the market (e.g. Ascorbyl glucoside, arbutins, plant extracts, kojic acid, Vitamin C derivatives), however these often show formulation or penetration constraints, have low in-vivo efficacy and/or give rise to safety concerns. As consumers are becoming increasingly aware of the toxicity issues related to some of these whitening agents, there is an ongoing need for effective and safe whitening actives considered as "natural" and without major side effects.

Resveratrol, also referred to as 3,4',5-trihydroxystilbene, is a naturally occurring molecule found in red grapes and hence red wine, peanuts, knotweed, raspberries, blueberries, and certain other plant berries. This compound has been the subject of intense research in recent years. Scientific reports are increasingly demonstrating the multi-functional benefits of resveratrol. Resveratrol is reported to be an extremely potent anti-oxidant, a modulator of genetic expression via signal transduction, an inhibitor of inflammatory mediators, to have phytohormonal benefits, and to reduce the synthesis of melanine. Such combination of biological functions and the cosmetic effects makes resveratrol a unique active ingredient for personal care products.

Despite all the above biological properties and its superior skin whitening effects, the formulation of resveratrol into cosmetic compositions poses a set of challenges. One problem with resveratrol is that it is generally unstable in cosmetic compositions (such as O/W or W/O emulsions) as it induces phase separation in emulsions and promotes color change from white to yellowish-brown. Accordingly, so far its use in cosmetic formulations is restricted to very small amounts. Furthermore, resveratrol tends to precipitate (crystallize) in cosmetic compositions containing water.

For the above outlined reasons the incorporation of high content resveratrol is believed only to be feasible in substantially water-free cosmetic compositions. Furthermore, different non-aqueous polar organic solvents such as PEG-solvents have been used to solubilize resveratrol before adding into O/W or W/O emulsions. However the amounts of solvents reported are extremely high. (see e.g. US 2007/0225360, EP123457, US 2002/0173472). Such high levels of solvents however may cause skin irritation if applied on damaged or sensitive skin. Moreover, high solvent levels are known to diminish the aesthetics in tactile properties such as skin feeling.

Thus, there is an ongoing need to overcome the drawbacks of the prior art and to find an acceptable solubilizer for resveratrol as well as a robust and stable emulsion system.

Surprisingly it has been found that resveratrol can be solubilized in a liquid phosphate ester surfactant. Furthermore it has been found that the thus solubilized Resveratrol in combination with at least one cosmetic oil can serve as self emulsifying cosmetic base, i.e. the addition of the self emulsifying cosmetic base to water leads to the spontaneous formation of an emulsion, allowing the incorporation of high amounts of solubilized resveratrol into fluid compositions.

Thus, in a first embodiment the invention relates to a fluid composition comprising water and a self-emulsifying cosmetic base consisting of resveratrol, a liquid phosphate ester surfactant, at least one cosmetic oil, and optionally a co-emulsifier.

The term "self-emulsifying" means that the cosmetic base forms an emulsion/microemulsion in situ when in contact with water.

The term "fluid" refers to a water-like consistency which characterizes an ability to flow under its own weight and in particular to spread when deposited on a flat surface.

In another embodiment, the invention relates to a process for the preparation of a fluid composition, said process comprising the step of dissolving resveratrol in a liquid phosphate ester surfactant and at least one cosmetic oil, optionally in the presence of a co-emulsifier (in order to form the self emulsifying cosmetic base) followed by addition of the resulting solution to water. The temperature for the preparation of the self emulsifying cosmetic base is not critical. Preferably, the temperature for the solubilisation of the resveratrol is selected in the range of 20-60° C., most preferably in the range of 30-40° C. The addition of the self emulsifying cosmetic base to water can either be done directly after preparation or after cooling if heat had been applied.

In a further embodiment, the invention relates to the use of a liquid phosphate ester surfactant as solubilizer for resveratrol.

Preferably, the fluid composition of the present invention consists of 20-80 wt.-% of water, 20-80 wt.-% of the self-emulsifying cosmetic base and up to 10 wt.-% of remainder ingredients, wherein the amount of all components sums up to 100 wt.-%.

In all embodiments of the invention, preferably the total amount [sum] of phosphate ester surfactant and co-emulsifier in the fluid composition according to the present invention is at least 6 wt.-% based on the total weight of the fluid composition. Preferably, the total amount [sum] of phosphate ester surfactant and co-emulsifier is selected in the range of 7-30 wt.-%, most preferably in the range of 7.5-20 wt.-% based on the total weight of the fluid composition.

It is furthermore advantageous if the self-emulsifying cosmetic base consists of
  (i) 5-60 wt.-%, preferably 8-50 wt.-%, most preferably 10-30 wt.-% of a phosphate ester surfactant,
  (ii) 0-40 wt.-%, preferably 0-30 wt.-%, most preferably 0-25 wt.-% of a co-emulsifier
  (iii) 40-90 wt.-%, preferably 50-80 wt.-%, most preferably 60-75 wt.-% of at least one cosmetic oil and,
  (iv) 0.01-7 wt.-% of resveratrol
wherein the amount of all components sums up to 100 wt.-%. Preferably the total amount [sum] of phosphate ester surfactant and co-emulsifier in the self-emulsifying cosmetic base is at least 15 wt.-%. More preferably the total amount [sum] of phosphate ester surfactant and co-emulsifier is selected in the range of 20-50 wt.-% and the amount of the at least one cosmetic oil is selected in the range of 50-80 wt.-% based on the total weight of the self-emulsifying cosmetic base. Most preferably the total amount [sum] of phosphate ester surfactant and co-emulsifier is selected in the range of 25-35 wt.-% and the amount of the at least one cosmetic oil is selected in the range of 60-75 wt.-% based on the total weight of the self-emulsifying cosmetic base.

Resveratrol [CAS501-36-0, CA Name: 5-[(1E)-2-(4-hydroxyphenypethenyl]-1,3-Benzenediol] is e.g. commercially available at DSM Nutritional Products Ltd.

In all embodiments of the present invention the amount of resveratrol is selected such that it is completely solubilized at ambient temperature (i.e. 20° C.) in the phosphate ester surfactant and the cosmetic oil and, if present, the co-emulsifier.

The maximum amount of resveratrol which can be incorporated into the fluid compositions according to the present invention may depend on the phosphate ester surfactant, co-emulsifier and cosmetic oil used but can easily adjusted by a person skilled in the art.

In all embodiments of the present invention the amount of resveratrol in the fluid compositions is preferably selected in the range of about 0.01 to 5 wt.-%, more preferably in the range of 0.05 to 2 wt.-%, most preferably in the range of 0.1 to 1 wt.-% based on the total weight of the fluid composition.

The "term co-emulsifier" refers to any emulsifier which is either liquid at ambient temperature (20° C.) or which is soluble in the phosphate ester surfactant. Preferably, in all embodiments of the present invention the co-emulsifier is liquid at ambient temperature (20° C.). Particular suitable co-emulsifiers for the purpose of the present invention are liquid non-ionic emulsifiers, such as preferably polyethylene glycol-based emulsifiers such as most preferably Laureth-7.

If present, the amount of co-emulsifier in the fluid compositions according to the present invention is preferably selected in the range of 1 to 30 wt.-%, more preferably in the range of 2 to 20 wt.-%, most preferably in the range of 3 to 15 wt.-% based on the total weight of the fluid composition.

Suitable cosmetic oils according to the present invention are all cosmetic oils conventionally used in cosmetic fluid compositions such as in particular capric/caprylic triglyceride, isopropyl palmitate and isopropylpalmitate as well as mixtures thereof. Further suitable oils are natural polar oils.

In all embodiments of the present invention the amount of the at least one cosmetic oil in the fluid composition according to the present invention is selected in the range of 5 to 70 wt.-%, preferably in the range 10 to 60 wt.-%, most preferably in the range 15 to 55 wt.-% based on the total weight of the fluid composition.

The "term liquid phosphate ester surfactant" refers to any phosphate ester surfactant which is liquid at ambient temperature (20° C.). Particular suitable liquid phosphate ester surfactants according to the present invention are trilaureth-4 phosphate (e.g. available as Hostaphat KL 340D or SILAPHOS® TE 340), C8-C10 Phosphate (e.g. available as Crodafos™ 810A), PPG-5-Ceteth-10 Phosphate (e.g. available as Crodafos™ C10/5A), Cetoleth-5 Phosphate (e.g. available as Crodafos™ CO5A), Deceth-4 Phosphate (e.g. available as Crodafos™ D4A), Glycereth-26 Phosphate (e.g. available as Crodafos™ G26A), Oleth-5 Phosphate and Dioleyl Phosphate (e.g. available as Crodafos™ HCE), Potassium C12-12 Alkyl Phosphate (e.g. available as Crodafos™ 1213K), TEA C12-13 Alkyl Phosphate (e.g. available as Crodafos™ 1213T), C9-15 Alkyl Phosphate (e.g. available as Crodafos™ M915A), Oleth-10 Phosphate (e.g. available as Crodafos™ 010A), DEA Oleth-10 Phosphate (e.g. available as Crodafos™ 010D), Oleth-3 Phosphate (e.g. available as Crodafos™ 03A), DEA Oleth-3 Phosphate (e.g. available as Crodafos™ 03D), Trideceth-10 Phosphate (e.g. available as Crodafos™ T10A), Trideceth-5 Phosphate (e.g. available as Crodafos™ T5A) or Trideceth-6 Phosphate (e.g. available as Crodafos™ T6A). Most preferably in all embodiments of the present invention the phosphate ester surfactant is trilaureth-4 phosphate [CAS 31800-90-5].

The phosphate ester surfactant is generally present in the fluid compositions according to the invention in proportions ranging from 1 to 50 wt.-%, preferably from 2 to 30 wt.-%, most preferably from 3 to 25 wt.-% based on the total weight of the fluid composition.

In all embodiments of the invention the ratio (w/w) of the phosphate ester surfactant such as trilaureth-4 phosphate to resveratrol is advantageously selected in the range of 200:1 to 1:1, preferably in the range of 50:1 to 2:1 such as in the range of 10:1 to 2.5:1.

In all embodiments of the invention the ratio (w/w) of co-emulsifier (if present) to phosphate ester surfactant is advantageously selected in the range of 10:1 to 1:10 such as preferably in the range of 5:1 to 1:5.

In a particular embodiment, the fluid composition according to the present invention consists of
(i) 20-80 wt.-% of water
(ii) 1-45 wt.-% of a liquid phosphate ester surfactant,
(iii) 15-55 wt.-% of a cosmetic oil,
(iv) 0-20 wt.-% of a liquid non-ionic co-emulsifier,
(v) 0.05-5 wt.-% of resveratrol and optionally
(vi) up to 5 wt.-% of remainder ingredients
wherein the sum of all ingredients sum up to 100 wt.-% and wherein the total amount of phosphate ester surfactant and co-emulsifier is at least 6 wt.-% based on the total weight of the fluid composition.

In one particular advantageous embodiment, the fluid compositions according to the present invention are free of a co-emulsifier and the amount of phosphate ester surfactant is selected in the range of 7-30 wt.-%, preferably in the range of 7.5-20 wt.-%.

In another particular advantageous embodiment, the fluid compositions according to the present invention comprise a co-emulsifier, the total amount [sum] of phosphate ester surfactant and co-emulsifier is selected in the range of 7-30 wt.-% based on the total weight of the fluid composition and the ratio of co-emulsifier to phosphate ester surfactant is selected in the range of 10:1 to 1:10. Even more preferably, the total amount [sum] of phosphate ester surfactant and co-emulsifier is selected in the range of in the range of 7.5-25 wt.-% based on the total weight of the fluid composition and the ratio of co-emulsifier to phosphate ester surfactant is selected in the range of 5:1 to 1:5.

In all embodiments of the present invention most preferably the phosphate ester surfactant is trilaureth-4 phosphate, the cosmetic oil is capric/caprylic triglyceride and, if present, the co-emulsifier is Laureth-7.

The term "fluid composition" as used herein refers in particular to cosmetic compositions which are fluid and which can be topically applied to mammalian keratinous tissue such as e.g. human skin or hair, particularly human skin.

Suitable remainder ingredients according to the present invention encompass skin active ingredients such as e.g. ingredients for skin lightening; tanning prevention; treatment of hyperpigmentation; preventing or reducing acne; preventing or reducing wrinkles and/or lines; preventing or reducing atrophy and/or inflammation as well as agents to improve elasticity and skin barrier. Further suitable remainder ingredients are usual cosmetic adjuvants and additives, such as preservatives/antioxidants, UV-filter substances, chelators, organic solvents, silicones, thickeners, softeners, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, antifoaming agents, or any other ingredients usually formulated into cosmetic compositions. Such cosmetic ingredients commonly used in the skin care industry, which are suitable for use in the fluid compositions of the present invention are e.g. described in the CTFA Cosmetic Ingredient Handbook, Second Edition (1992) without being limited thereto. The necessary amounts of the remainder ingredients can, based on the desired product, easily be determined by the skilled person.

Preferred examples of skin active ingredients are vitamin C (ascorbic acid) and/or its derivatives (e.g. ascorbyl phosphate such as Stay C (sodium ascorbyl monophosphate) from DSM Nutritional Products Ltd.), vitamin A and/or its derivatives (e.g., retinoid derivatives such as retinyl palmitate or retinyl propionate), vitamin E and/or its derivatives (e.g., tocopherol acetate), vitamin $B_6$, vitamin $B_{12}$, biotin, co-enzyme Q10, EGCG, hydroxytyrosol and/or olive extract, shea butter, algae extract, cocoa butter, aloe extract, jojoba oil, echinacea extract, chamomile extract, Glycyrrhetinic Acid, Glycyryca Glabra extract, in particular vitamin E and/or its derivatives, shea butter, algae extract, cocoa butter, aloe extract and/or vitamin A and/or its derivatives, Alpaflor plant extracts by DSM Nutritional products, The additional cosmetically active ingredient is typically included in an amount of at least 0.001 wt. % based on the total weight of the fluid composition. Generally, an amount of about 0.001 wt. % to about 30 wt. %, preferably from about 0.001 wt. % to about 10 wt. % of an additional cosmetically active agent is used.

A vitamin E derivative for use in the present invention is tocopheryl acetate. Tocopheryl acetate may be present in the fluid composition in an amount from about 0.05 wt.-% to about 25 wt.-%, in particular 0.5 wt.-% to 5 wt.-%. Another vitamin E derivative of interest is tocopheryl linoleate. Tocopheryl linoleate may be present in the fluid compositions in an amount from about 0.05 wt.-% to about 25 wt.-% in particular 0.05 wt.-% to 5 wt.-%.

Vitamin A and/or its derivatives in particular retinoid derivatives such as retinyl palmitate or retinyl propionate is preferably used in the fluid compositions according to the invention in an amount of 0.01-5 wt.-%, in particular 0.01-0.3 wt.-%.

Suitable UV-filter substance to be incorporated into the fluid compositions according to the present invention are conventional UVA and/or UVB and/or broad spectrum UV-filter substances known to be added into topical compositions such as cosmetic or dermatological sun care products. Such UV-filter substances comprise all groups which absorb light in the range of wavelengths 400 nm to 320 nm (UVA) and 320 nm to 280 nm (UVB) or of even shorter wavelengths (UVC) and which are or can be used as cosmetically acceptable UV-filter substances. Such UV-filter substances are e.g. listed in the CTFA Cosmetic ingredient Handbook or "The Encyclopedia of Ultraviolet Filters" (ISBN: 978-1-932633-25-2) by Nadim A. Shaath.

A particular suitable preservative to be used in the fluid composition according to the invention is methylisothiazolinone.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

The fluid compositions according to the invention have a pH in the range of 3-10, preferably in the range of pH of 4-8, most preferred in the range of pH 4-7.

The following examples are provided to further illustrate the compositions and effects of the present invention. These examples are illustrative only and are not intended to limit the scope of the invention in any way.

Example 1

The self emulsifying cosmetic bases as outlined in table 1 were prepared by mixing all ingredients at a moderate temperature (30-40° C.) whereby a clear solution was formed.

TABLE 1

| Self emulsifying cosmetic base | | | | | |
|---|---|---|---|---|---|
| | I | II | III | IV | V |
| | wt.-% | | | | |
| Phosphate ester surfactant: Trilaureth-4 Phosphate | 5 | 10 | 15 | 20 | 25 |
| Co-emulsifier: Laureth-7 | 25 | 20 | 15 | 10 | 5 |
| Cosmetic oil: Capric/caprylic triglyceride | 68 | 68 | 68 | 68 | 68 |
| Resveratrol | 2 | 2 | 2 | 2 | 2 |

Afterwards, the self emulsifying system was added to water in a ratio (w/w) of 1 to 3 and 3 to 1. In both cases spontaneously an aqueous emulsion was formed which upon separation (after >1 week) could be easily re-formed by mere shaking.

Example 2

A self emulsifying cosmetic base exempt of co-emulsifier was prepared by dissolving resveratrol in trilaureth-4 phosphate by continuous mixing at moderate temperature (30-40° C.). The clear solution was then added to the cosmetic oil and mixed. This self emulsifying cosmetic base was then added to water in the ratios shown in Table 3. In all cases spontaneously an aqueous emulsion was formed which upon separation (after >1 week) could be easily re-formed by mere shaking.

TABLE 2

| Self emulsifying cosmetic base | |
|---|---|
| Ingredient | wt.-% |
| Phosphate ester surfactant: Trilaureth-4 Phosphate | 30.0 |
| Resveratrol | 2.0 |
| Cosmetic oil: Capric/caprylic triglyceride | 68.0 |

TABLE 3

| Fluid composition | | | | |
|---|---|---|---|---|
| | I | II | III | IV |
| Self emulsifying cosmetic base | 30 wt % | 40 wt % | 50 wt % | 60 wt % |
| Water | 70 wt % | 60 wt % | 50 wt % | 40 wt % |

The invention claimed is:

1. A fluid composition comprising water and a self-emulsifying cosmetic base consisting of resveratrol, 1-45 wt. % of a liquid trilaureth-4 phosphate surfactant, 15-55 wt. % of at least one cosmetic oil, up to 10 wt. % of remainder ingredients, and 0-20 wt. % of a co-emulsifier.

2. The fluid composition according to claim 1, wherein the composition consists of 20-80 wt. % of water, and 20-80 wt. % of the self-emulsifying cosmetic base, wherein the amount of all components sums up to 100 wt. %.

3. The fluid composition according to claim 1, wherein the total amount of the liquid trilaureth-4 phosphate surfactant and the co-emulsifier is at least 6 wt. %, based on the total weight of the fluid composition.

4. The fluid composition according to claim 1, wherein the total amount of the liquid trilaureth-4 phosphate surfactant and the co-emulsifier is within a range of 7 to 30 wt. %, based on the total weight of the fluid composition.

5. The fluid composition according to claim 1, wherein the self-emulsifying cosmetic base consists of 5-60 wt. % of the liquid trilaureth-4 phosphate surfactant, 0-40 wt. % of the co-emulsifier, 40-90 wt. % of the cosmetic oil and 0.01-7 wt. % of the resveratrol, based on total weight of the self-emulsifying base, wherein the amount of all components sums up to 100 wt.-%.

6. The fluid composition according to claim 1, wherein the co-emulsifier is present in an amount of 1 to 30 wt. %, based on total weight of the fluid composition.

7. The fluid composition according to claim 1, wherein the co-emulsifier is a liquid non-ionic co-emulsifier.

8. The fluid composition according to claim 1, wherein the co-emulsifier is a polyethylene glycol-based emulsifier.

9. The fluid composition according to claim 8, wherein the co-emulsifier is Laureth-7.

10. The fluid composition according to claim 1, wherein the at least one cosmetic oil is selected from the group consisting of capric/caprylic triglyceride, isopropyl palmitate, isopropylpalmitate and mixtures thereof.

11. The fluid composition according to claim 1, wherein the resveratrol is present in an amount within a range of 0.01 to 5 wt. %, based on the total weight of the fluid composition.

12. The fluid composition according to claim 1, wherein the co-emulsifier and liquid trilaureth-4 phosphate surfactant are present in amounts to provide a ratio (w/w) of the co-emulsifier to the liquid trilaureth-4 phosphate surfactant of 10:1 to 1:10.

13. The fluid composition according to claim 1, wherein the liquid trilaureth-4 phosphate surfactant and the resveratrol are present in amounts to provide a ratio (w/w) of the liquid trilaureth-4 phosphate surfactant to the resveratrol of 200:1 to 1:1.

14. A process for the preparation of a fluid composition according to claim 1, wherein the process comprises:
(i) forming a resveratrol-containing solution by dissolving the resveratrol in the liquid trilaureth-4 phosphate surfactant and the at least one cosmetic oil, optionally in the presence of the co-emulsifier, followed by
(ii) adding the resulting resveratrol-containing solution of step (i) to water.

* * * * *